(12) United States Patent
Butterworth et al.

(10) Patent No.: US 10,444,174 B2
(45) Date of Patent: Oct. 15, 2019

(54) METHOD FOR TESTING A METAL DETECTION APPARATUS AND METAL DETECTION APPARATUS

(71) Applicant: Mettler-Toledo Safeline Ltd., Salford, Manchester (GB)

(72) Inventors: Daren Butterworth, Manchester (GB); Andrew Blackburn, Oldham (GB)

(73) Assignee: Mettler-Toledo Safeline Ltd., Salford-Manchester (GB)

( * ) Notice: Subject to any disclaimer, the term of this patent is extended or adjusted under 35 U.S.C. 154(b) by 100 days.

(21) Appl. No.: 15/807,327

(22) Filed: Nov. 8, 2017

(65) Prior Publication Data
US 2018/0136152 A1    May 17, 2018

(30) Foreign Application Priority Data

Nov. 11, 2016    (EP) .................................... 16198342

(51) Int. Cl.
| | |
|---|---|
| *G01N 27/02* | (2006.01) |
| *G01N 27/90* | (2006.01) |
| *G01V 3/10* | (2006.01) |
| *G01V 13/00* | (2006.01) |
| *G01R 27/26* | (2006.01) |
| *G01R 33/038* | (2006.01) |
| *G01R 33/06* | (2006.01) |

(52) U.S. Cl.
CPC ........ *G01N 27/023* (2013.01); *G01N 27/9013* (2013.01); *G01V 3/102* (2013.01); *G01V 3/104* (2013.01); *G01V 3/107* (2013.01); *G01V 13/00* (2013.01); *G01R 27/267* (2013.01); *G01R 33/0385* (2013.01); *G01R 33/066* (2013.01)

(58) Field of Classification Search
CPC ........ G08B 1/00; G01N 1/00; G01N 2201/00; G01R 1/00
See application file for complete search history.

(56) References Cited

U.S. PATENT DOCUMENTS

| | | |
|---|---|---|
| 5,160,885 A | 11/1992 | Hannam et al. |
| 5,994,897 A | 11/1999 | King |
| 8,587,301 B2 | 11/2013 | Derungs |

(Continued)

FOREIGN PATENT DOCUMENTS

JP    2005-292095 A    10/2005

*Primary Examiner* — Huy Q Phan
*Assistant Examiner* — Temilade S Rhodes-Vivour
(74) *Attorney, Agent, or Firm* — Standley Law Group LLP; Jeffrey S. Standley; Stephen L. Grant (57) ABSTRACT

A metal detection apparatus (9) is tested with a test device (7) having at least one test article (79), movable through a detection zone (60). The test article is moved through the detection zone along a first transfer axis (ca) and a first input signal is measured. A first threshold (th1) is determined, where an amplitude of the first input signal exceeds the first threshold (th1). Then, an identical test article is moved through the detection zone along a further transfer axis (ta; ... ) and a further input signal is measured and a further threshold (th2; ... ) is determined, where an amplitude of the further input signal exceeds the further threshold (th2; ... ). The first or further threshold (th1; th2; ... ) is selected in the signal processing path (4) whenever the test article is moved along the related transfer axis (ca; ta; ... ).

16 Claims, 7 Drawing Sheets

(56) References Cited

U.S. PATENT DOCUMENTS

| | | | |
|---|---|---|---|
| 2003/0127609 A1* | 7/2003 | El-Hage | G01N 21/253 250/574 |
| 2005/0253711 A1* | 11/2005 | Nelson | F41H 11/136 340/552 |
| 2006/0228049 A1* | 10/2006 | Gensolen | G06T 7/20 382/309 |
| 2008/0297158 A1* | 12/2008 | Heger | G01V 3/107 324/326 |
| 2012/0314092 A1* | 12/2012 | Chu | G01N 15/1463 348/207.1 |
| 2015/0142353 A1* | 5/2015 | Cabret | G01D 5/2291 702/64 |
| 2015/0234075 A1* | 8/2015 | Moore | G01V 3/105 324/225 |
| 2017/0176388 A1 | 6/2017 | Rigby | |

* cited by examiner

METHOD FOR TESTING A METAL DETECTION APPARATUS AND METAL DETECTION APPARATUS

CROSS-REFERENCE TO RELATED APPLICATIONS

This application claims priority to European application EP 16198342.4, filed on 11 Nov. 2016, the content of which is incorporated by reference as if fully recited herein.

TECHNICAL FIELD

The disclosed embodiments relate to a method for testing a metal detection apparatus and a metal detection apparatus that operates under such a method.

BACKGROUND

A metal detection apparatus is used to detect and reject unwanted metal contamination. When properly installed and operated, it will help reducing metal contamination and improving food safety. Most modern metal detectors utilise a search head comprising a "balanced coil system". Detectors of this design are capable of detecting all metal contaminant types including ferrous, nonferrous and stainless steels in a large variety of products such as fresh and frozen products.

The metal detection apparatus typically comprises a metallic enclosure, having entrance and exit apertures with cross-sectional areas of different or equal size defining a travel path inside the enclosure along which an object under inspection moves.

A metal detection apparatus that operates according to the "balanced coil"-principle typically comprises three coils that are wound onto a non-metallic frame or yoke. The coil system comprises at least one transmitter coil and at least one first and at least one second receiver coil; the respective receiver coils bounding a detection zone inside the enclosure between the entrance and exit apertures. The detection zone has a cross-sectional profile that varies or is constant along the travel path. Systems with cylindrical detection zones typically use coils having identical dimensions with the transmitter coil centred between the two receiver coils. Systems with conical detection zones use coils that differ in size from one another typically with the transmitter coil being off-centred between the two receiver coils. In both systems the coils are arranged such that, when the at least one transmitter coil is energized by an alternating electric current, the electromagnetic field generated thereby induces a first voltage in the first receiver coils and a second voltage in the second receiver coil, the first and second voltages cancelling each other out when there is no metal present in the object under inspection.

As a particle of metal passes through the coil arrangement, the high frequency field is disturbed first near one receiver coil and then near the other receiver coil. While the particle of metal is conveyed through the receiver coils the voltage induced in each receiver coil is changed. This change in balance results in a signal at the output of the receiver coils that can be amplified, processed and subsequently be used to detect the presence of the metal contamination.

The signal processing channels typically split the received signal into two separate components that are 90° apart from one another. The resultant vector has a magnitude and a phase angle, which is typical for the products and the contaminants that are conveyed through the coil system. In order to identify a metal contaminant, "product effects" need to be removed or reduced. If the phase of the product is known then the corresponding signal vector can be reduced. Eliminating unwanted signals from the signal spectrum thus leads to higher sensitivity for signals originating from contaminants.

Methods applied for eliminating unwanted signals from the signal spectrum therefore exploit the fact that the product, the contaminants and other disturbances, have different influences on the magnetic field so that the resulting signals differ in phase.

Distinguishing between the phases of the signal components of different origin by means of a phase detector allows obtaining information about the product and the contaminants. A phase detector, e.g. a frequency mixer or analogue multiplier circuit, generates a voltage signal which represents the difference in phase between the signal input, such as the signal from the receiver coils, and a reference signal provided by the transmitter unit to the receiver unit. Hence, by selecting the phase of the reference signal to coincide with the phase of the product signal component, a phase difference and a corresponding product signal is obtained at the output of the phase detector that is zero. In the event that the phase of the signal components that originate from the contaminants differ from the phase of the product signal component, then the signal components of the contaminants can be detected. However, in the event that the phase of the signal components of the contaminants is close to the phase of the product signal component, then the detection of contaminants fails, since the signal components of the contaminants are suppressed together with the product signal component.

In known systems, the transmitter frequency is therefore selectable in such a way that the phase of the signal components of the metal contaminants will be out of phase with the product signal component.

U.S. Pat. No. 8,587,301 B2 discloses a method for operating a metal detection system that allows determining a preferable transmitter frequency with which signal components of smallest sized metal particles differ most in phase and amplitude from the phase and amplitude of a product signal.

Hence, for testing and optimising a metal detection apparatus tests with different contaminants need to be performed, which is however time-consuming. Furthermore, tuning should be performed regularly particularly in view of the frequent changes of the processed product.

European Patent Application EP15200786.0 discloses a testing device for testing a metal detection apparatus, in which one or more test articles are passed along test axes in parallel or equally inclined to a product axis along which products travel through a detection zone. Each test article is embedded in a slug, which can move freely within a guide tube from one end to the other. Evaluation of the signals induced by the test articles allows checking the sensitivity of the metal detection apparatus.

Transferring the test articles along the test axis, which is offset from the product axis, allows testing the metal detection apparatus while products are transferred. A disadvantage of such a test device is that the sensitivity of the metal detection apparatus is not measured in other regions of the detection zone, which may be more critical than the region, in which the test device is installed.

For different regions of the detection zone which exhibit different sensitivities, the user of the apparatus may however use test articles, which are adapted to the sensitivity in the specific region of the detection zone. A single test article, e.g. as delivered by the manufacturer of the metal detection apparatus however is not suitable for performing tests in regions of the detection zone, which exhibit different sensitivities.

SUMMARY OF THE INVENTION

The present invention is therefore based on the object of providing an improved method for testing a metal detection apparatus and an improved metal detection apparatus that is operating according to this method.

The inventive method shall allow testing the sensitivity of a metal detection apparatus over the complete detection zone or in selected regions that are critical for the proper performance of the metal detection apparatus.

In particular, with the inventive method the metal detection apparatus shall be testable under worst-case conditions with a single test article.

Furthermore, with the inventive method it shall be possible to optimise the performance of the metal detection apparatus practically without additional effort for all contaminants possibly occurring in the processed products.

The inventive apparatus shall allow conveniently performing the test with the least effort. Further, it shall be possible to implement the inventive method in any metal detection system, even if it is already in use.

The above and other objects of the present invention are achieved by an improved method for testing a metal detection apparatus as defined in the appended claims, as well as a metal detection apparatus operating according to this method as also defined in the claims.

The method allows testing a metal detection apparatus with entrance and exit apertures adjoining a transfer channel, along which products are movable through a coil system that defines a detection zone and comprises a transmitter coil and a first and a second receiver coil dimensioned such that a current applied to the transmitter coil induces a first coil signal in the first receiver coil and a second coil signal in the second receiver coil, which first and second coil signals do not compensate one another when metal is present in the transferred products, which causes an input signal within a signal processing path of the metal detection apparatus, and with at least one test device that comprises at least one test article that is movable through the detection zone.

The method comprises the steps of moving the test article through the detection zone along a first transfer axis and measuring a first input signal;

moving an identical test article, preferably the same test article, through the detection zone along a second or further transfer axis and measuring a second or further input signal;

determining a first threshold adapted to the test article moved along the first transfer axis such that the amplitude of the first input signal exceeds the first threshold;

determining a second or further threshold adapted to the test article moved along the second or further transfer axis such that the amplitude of the second or further input signal exceeds the second or further threshold; and selecting said first, second or further threshold in the signal processing path whenever the test article is moved along the related first, second or further transfer axis.

The inventive method allows testing the metal detection apparatus with a single test article in various regions of the detection zone so that the performance of the metal detection apparatus can fully be tested, even with a single test device and a single test article.

The inventive method allows in particular testing the performance of the metal detection apparatus in regions of the detection zone which exhibits low or least sensitivity. Hence, the inventive method is not limited to testing the metal detection apparatus in a region of the detection zone with high sensitivity; while testing in other regions is neglected, in which sensitivity might be insufficient due to a malfunction or improper calibration.

By testing the metal detection apparatus in a region of reduced sensitivity, preferably in the region of least sensitivity, the presence of the required performance can be verified. False-positive testing can be avoided.

Furthermore, testing the metal detection apparatus can be performed with a single test article or with a plurality of identical test articles in a plurality of regions of the detection zone, which exhibit different sensitivities. For complete testing of the metal detection apparatus the user can therefore use a single test article or a set of test articles with numerous identical test articles.

Still further, preferably at least one first, at least one second or at least one further threshold is determined at least for the first test article for the related first, second and/or further transfer axis and for at least a first and a second operating frequency. Hence, for a set of operating frequencies a corresponding set of thresholds is provided.

Tests can be performed manually or automatically. In the inventive metal detection apparatus a suitable threshold is automatically selected from a set of thresholds predetermined for different regions of the detection zone. Further, a test device may automatically be moved between positions, in which a test article may be moved along a related transfer axis each for automatically testing the metal detection apparatus in specific regions of the detection zone.

In preferred embodiments, a set with test articles is provided, which have different properties and which can be applied in one or more regions of the detection zone that exhibit an approximately even sensitivity. The test article may be of any type, including ferrous, non-ferrous (e.g. aluminium) and non-magnetic stainless steel type. The same set of test articles can be applied to any transfer axis or region with a specific sensitivity after suitable thresholds have been predetermined.

Different test articles of a set of test articles may be moved sequentially along the same transfer axis or may be moved along different transfer axes in which the sensitivity for a specific test article is about equal. In a first embodiment, for each transfer axis or region with equal sensitivity the related first, second or further threshold margin or threshold is determined for the test article, which provides the input signal with the smallest amplitude. Consequently, if the test article, which provides the lowest signal, can be detected then it is assured that the other test articles, which provide higher signals, can also be detected.

In another important embodiment, a threshold is determined for each one of the test articles of the set of test articles. Testing is then performed preferably for every test article of the set of test articles for various frequencies, thus determining a frequency range, in which the determined threshold is exceeded. Based on the determined frequency range for each test article, the metal detection apparatus may be optimised, e.g. by selecting the centre frequency of the determined frequency range or intersections of two or more frequency regions. This process may be performed automatically without intervention of the user.

Hence, with a set of test articles sensitivity of the metal detection apparatus can be tested more precisely for all contaminants, which may occur in a product. As described, testing can be combined with optimising the metal detection apparatus. In the event that a test fails an alarm signal or report may be generated or corrective measures may automatically be taken, e.g. by stepping the transmitter frequency and repeating the test until a related threshold is exceeded. In the event that the threshold is not exceeded with various transmitter frequencies, an enhanced report can be issued. Due to the provision of predetermined thresholds overall tests can be executed efficiently and with reduced effort.

In a further preferred embodiment, a first margin and a first threshold are determined for a first transfer axis, for which the test article or the set of test articles provides an input signal with the smallest amplitude or corresponding input signals with the smallest amplitudes. Second or further margins for the second or further transfer axes are then determined depending on the first margin or the first threshold.

Accordingly, a plurality of tests for different transfer axes is or may be performed; whereafter said first transfer axis is determined by comparing the amplitudes of the related input signals and the transfer axis is selected for which the smallest input signal has been recorded. Alternatively, since the centre axis of the detection zone, which traverses the entrance aperture and the exit aperture at their centre points, typically exhibits the lowest sensitivity, the centre axis can be selected as the first transfer axis.

The second or further thresholds for the second or further transfer axes may then be determined in different ways.

The second or further second or further thresholds for the second or further transfer axes are preferably determined by multiplying the first threshold with a weighting factor q, which preferably corresponds to the ratio of the amplitudes of the input signals measured for a test article for the related second or further transfer axis compared to the amplitude of the input signal measured for the first transfer axis.

As an alternative, the second or further thresholds for the second or further transfer axes are determined by multiplying the first margin with a weighting factor q, which preferably corresponds to the ratio of the amplitudes of the input signals measured for a test article for the related second or further transfer axis compared to the amplitude of the input signal measured for the first transfer axis, in order to obtain a second or further margin by which the input signals measured for the related second or further transfer axis exceed the second or further thresholds. The second or further thresholds are therefore determined by subtracting the calculated second or further margins from the amplitudes of the input signals measured for a test article for the related second or further transfer axis.

Hence, for regions of higher sensitivity, the threshold margins are preferably increased, most preferably proportionally to the increased sensitivity or the ratio of the signal strength measured.

The inventive method may be applied in any metal detection system, in which products traverse a detection zone, e.g. horizontally or vertically. In preferred embodiments, the coil system defines a conical or cylindrical detection zone or a detection zone with a rectangular cross-section. One or a plurality of different test articles may be moved along the first transfer axis or along a second or further transfer axis, which are test axes located inside or outside the coil system peripherally to the detection zone.

In preferred embodiments the different second and further transfer axes are arranged equidistant from the first axis and arranged in parallel or equally inclined relative to the first axis. In this way with a plurality of test devices the performance of the metal detection apparatus can be tested over the whole range of contaminants that are potentially present in products.

The test devices preferably comprise a guiding device, which is designed for guiding the test article along the related first, second or further transfer axis. A specific test device may be assigned to every transfer axis or at least one test device may be movable between at least two of the transfer axes for performing the tests.

The guiding device is preferably a tube, in which the test article can be moved forth and back driven by air pressure or gravity.

In further preferred embodiments, the test device is mounted on a holding device with which the test device can be moved between a first position, in which the test article is movable along the first transfer axis, and a second or further position, in which the test article is movable along the second or further transfer axis.

The holding device is preferably coupled to a drive unit, with which the holding device is movable or moved between the first, second or further positions.

The metal detection apparatus preferably comprises a control unit, with which the drive unit is controlled and/or the first, second or further threshold is applied in the signal processing path according to the position of the test device.

In another preferred embodiment the metal detection apparatus comprises at least one position sensor, with which the position of the test device is sensed and signalled to a control unit, which selects said first, second or further threshold in the signal processing path whenever the test article is moved along a related first, second or further transfer axis.

In the event that the test device is moved automatically under the control of the drive unit, the drive unit may also automatically set the corresponding threshold. However, in case that the drive device is moved manually; then the position reached by the test device is preferably sensed by a related position sensor.

BRIEF DESCRIPTION OF THE DRAWINGS

Some of the objects and advantages of the present invention have been stated, others will appear when the following description is considered together with the accompanying drawings, in which:

as shown in FIG. 2;

as shown in FIG. 1 or FIG. 2;

DETAILED DESCRIPTION OF THE PREFERRED EMBODIMENTS

Figure 1:
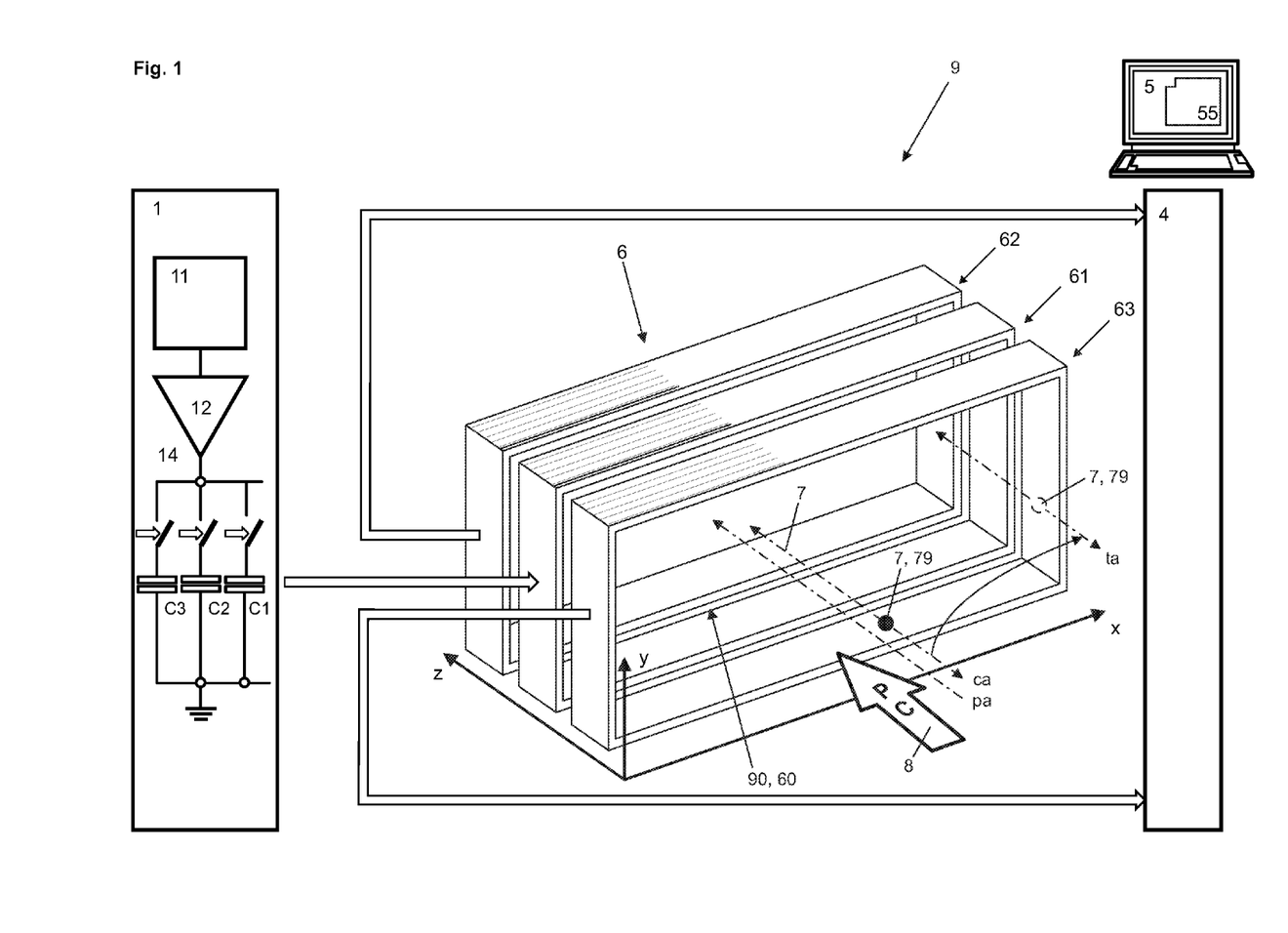
FIG. 1 shows schematically a metal detection apparatus 9 that is operating according to the inventive method and that comprises at least one test device 7 with a test article 79, which test device 7 is movable from a first position, in which the test article 79 is movable along a first transfer axis or centre axis ca, and a second position, in which the test article 79 is movable along a second transfer axis or test axis ta.

FIG. 1 schematically shows an inventive metal detection system 9 that comprises a transmitter unit 1, a balanced coil system 6 with a transmitter coil 61, a first and a second receiver coil 62, 63, a receiver unit 4 including a signal processing unit and a control unit 5 such as a standard computer system, that comprises standard interfaces, input devices and output devices, preferably a keyboard and a monitor and in which a program 55 is implemented, with which measurement processes, calibration processes and test processes are controllable. FIG. 1 further symbolically shows a conveyor 8, on which products P, which may comprise metal contaminants C, are transferred along a product axis pa through a transfer channel 90 of the metal detection apparatus 9 (see FIG. 2) and through a detection zone 60 delimited by the balanced coil system 6.

The transmitter unit 1 comprises a frequency generator 11 that provides a signal with an operating frequency to the input of a power amplifier 12 that operates for example according to class A or B standard. The output of the power amplifier 12 is connected to the transmitter coil 61 and selectively via a switch bank 14 to capacitors C1, C2, C3. With the selectable capacitors C1, C2, C3 the transmitter coil 61 can be tuned to a transmitter frequency selected by the control unit 5 at the frequency generator 11. The transmitter signal applied to the transmitter coil 61 induces a first coil signal in the first receiver coil 62 and a second coil signal in the second receiver coil 63, that do not compensate one another when metal C is present in the products P. Instead, when metal C is present in the transferred products P, the signals of the receiver coils 62, 63 provide a difference signal, which is processed as an input signal in the signal processing path of the receiver unit 4. The input signal is for example amplified and filtered in the receiver unit 4 and forwarded to the control unit 5. Preferably in the control unit 5 the input signal is compared with a threshold. In the event that the threshold is exceeded by the input signal a contaminant or test article is detected and signalled.

FIG. 1 further shows symbolically one or two test devices 7, which comprise a test article 79 that can be moved along a related transfer axis ca or ta. As shown in FIG. 5B, the test device preferably comprises a hollow tube 71 along which a test article 79 can travel forward and backward, preferably propelled by air pressure. A single test device 7 may be movable between a first transfer axis ca, such as the centre axis of the detection zone 60, and a second transfer axis ta, a test axis selected in the periphery of the detection zone 60. Alternatively, a first test device 7 with a first test article 79 may be firmly installed at the test axis ta, while a movable second test device 7 with a second test article 79 may be provided separately.

Hence, according to the invention the same test article 79 of a single test device 7 or identical test articles 79 of two or more test devices 7 can be used for test purposes, although sensitivities of the metal detection apparatus 9 in the region of the centre axis ca and the region of test axis ta are different. In order to ensure applicability of the same or identical test articles in different regions of the detection zone 60 individual thresholds are determined for every transfer axis ca and ta and the unique test article. For this purpose, the test article 79 is moved through the detection zone 60 along the first transfer axis ca and a first input signal is measured, for which a first threshold th1 is determined such that the amplitude of the first input signal exceeds the first threshold th1 by a first margin M1 (see FIG. 4). Then the same or an identical test article 79 is moved through the detection zone 60 along the second transfer axis ta and a second input signal is measured, for which a second threshold th2 is determined such that the amplitude of the second input signal exceeds the second threshold th2 by a second margin M2. Subsequently the determined first or second threshold th1; th2 is applied in the signal processing path of the receiver unit 4 whenever the test article 79 is moved along the related first or second transfer axis ca or ta. The related threshold th1 or th2 can be selected manually or automatically for the transfer axis ca or ta along which the test article 79 is currently moved. In preferred embodiments (see FIG. 6) the position of the test device 7 is detected by means of a position sensor 33.

In the event that a set of test articles 79 is used for testing the metal detection apparatus 9, then a threshold for a transfer axis may be determined for the test article 79 only, which provides the smallest signal, or for every test article 79 of the set of test articles 79. With the determined thresholds the metal detection apparatus 9 can be tested with little effort over the whole range of potential contaminants C. As well, by using the determined thresholds the metal detection apparatus 9 can be optimised for specific contaminants C. For different types of metal contaminants ranges of the transmitter frequencies can be determined, for which the related input signals exceed the related thresholds. In the event that two specific contaminants C are of interest, then a transmitter frequency is selected in the intersection of the frequency ranges determined for these contaminants C.

Hence, in preferred embodiments, at least one first, at least one second and/or at least one further threshold th1$x$, th1$y$; th2$x$, th2$y$; . . . is determined at least for the first test article 79 for the related first, second or further transfer axis ca; ta; . . . and for at least a first and a second operating frequency fx, fy. Most preferably, thresholds are provided for all or a part of the combinations of all test articles, all transfer axes and all operating frequencies.

Since all of these processes can be executed automatically, testing and optimising the metal detection apparatus 9 can be done quickly and with little effort.

Figure 2:
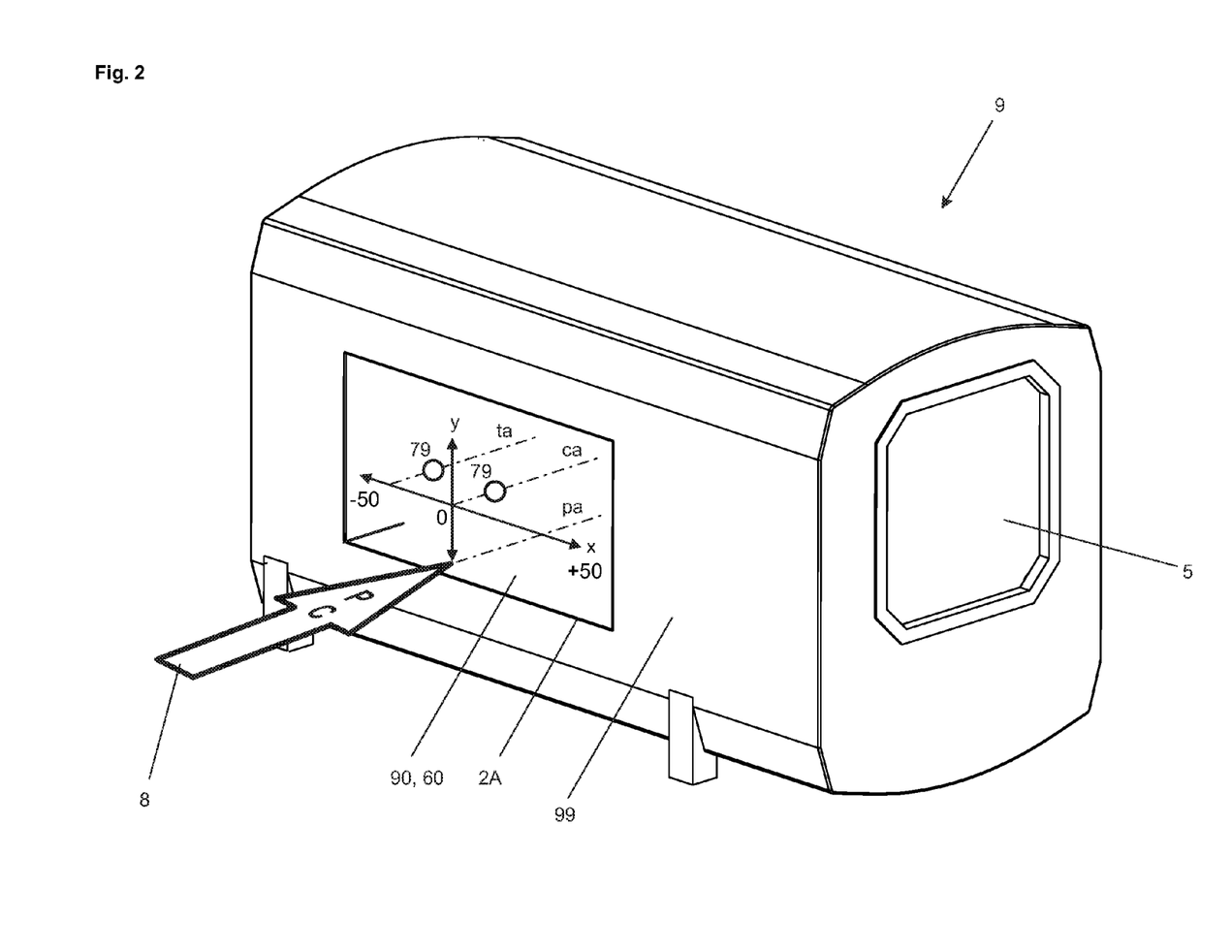
FIG. 2 shows a preferred embodiment of an inventive metal detection apparatus 9 of FIG. 1.

FIG. 2 shows a preferred embodiment of an inventive metal detection apparatus 9 of FIG. 1 with an integrated control unit 5 and a transfer channel 90 and a detection zone 60 with a rectangular cross-section. The first transfer axis, along which a test article 79 is movable, is the centre axis ca. The second transfer axis, along which a test article 79 is movable, is a test axis ta, which is offset by approx. 30 mm to the left of the centre axis ca.

Figure 3:
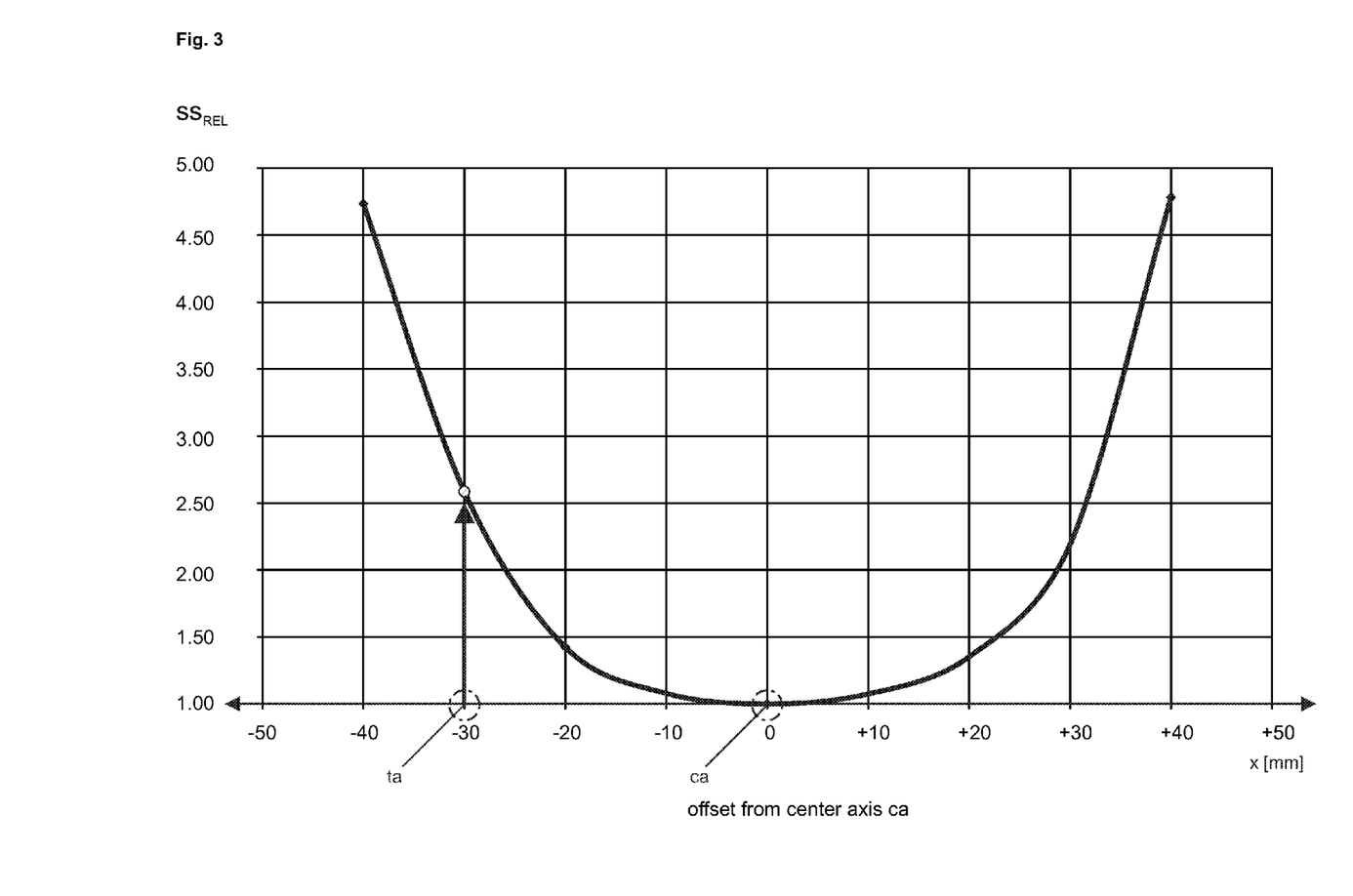
FIG. 3 shows a diagram of the relative signal strength recorded for a test article 79 that has been moved along a horizontal axis within the detection zone of a metal detection apparatus 9 e.g.

FIG. 3 shows a two-dimensional diagram of the relative signal strength recorded for a test article 79 that has been moved along a horizontal axis within the detection zone 60 of a metal detection apparatus 9 for example as shown in FIG. 2. The line recorded corresponds approximately to a parabola line of a parabola surface extending through the detection zone 60. The centre axis ca located at the vertex of the parabola extends perpendicular to the x-axis of the diagram. It can be seen that the relative signal strength ssREL is lowest at the centre point or centre axis ca and increases to the left and to the right therefrom. As shown in FIG. 2 a test axis ta is provided 30 mm to the left of the centre axis ca. Along this test axis the sensitivity or relative signal strength ssREL is increased by a factor of approximately 2.5. Accordingly, a first threshold th1 provided for the centre axis ca is multiplied preferably by a factor of 2.5 in order to obtain a threshold th2 for the test axis ta and the same or identical test article 79.

Figure 4:
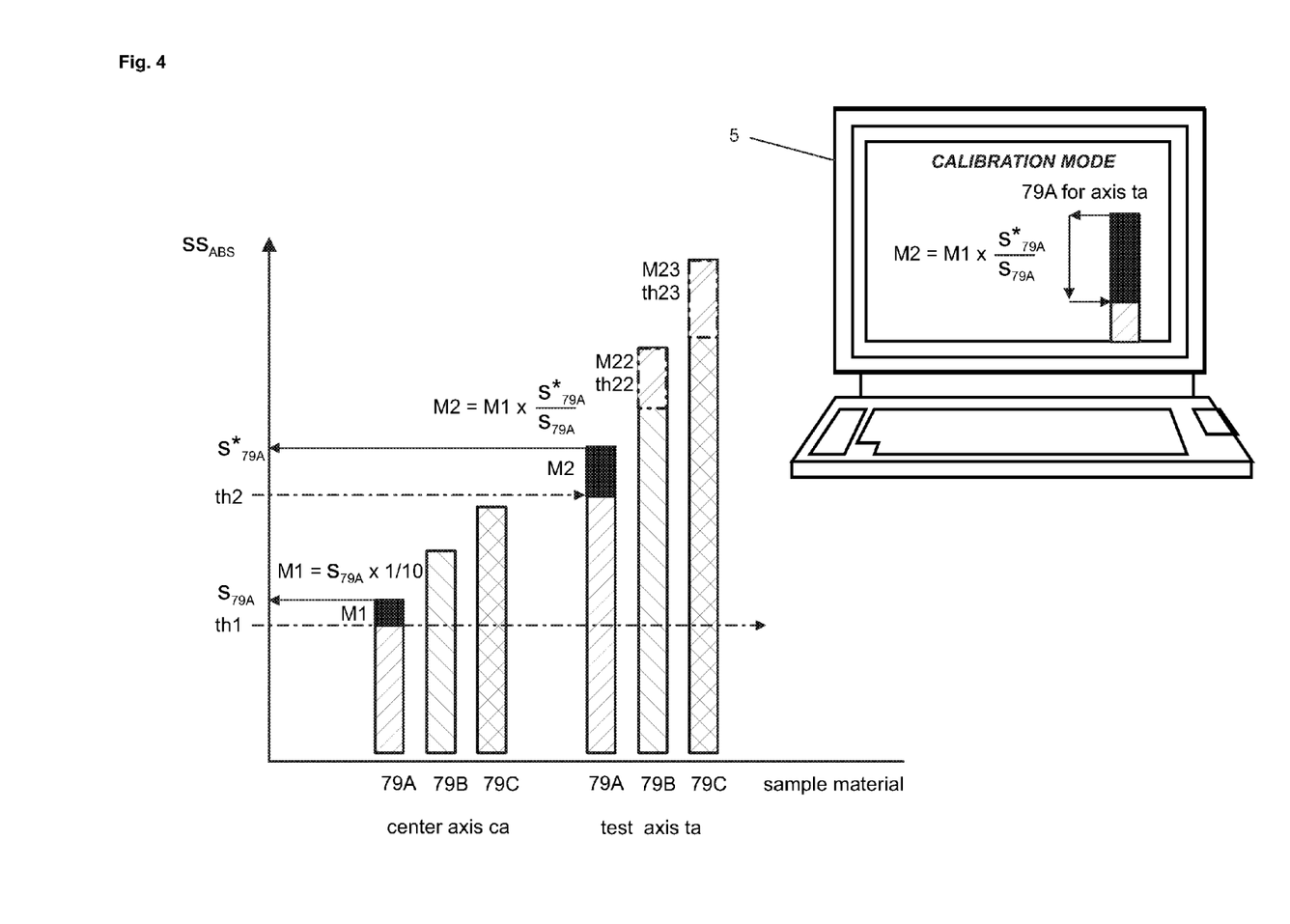
FIG. 4 shows signal amplitudes recorded for a set of three test articles 79A, 79B, 79C that have been moved first along the centre axis ca and then along the test axis ta of the metal detection apparatus 9 e.g.

FIG. 4 shows signal amplitudes recorded for a set of three test articles 79A, 79B, 79C that have been moved first along the centre axis ca and then along the test axis ta of the metal detection apparatus 9 e.g. as shown in FIG. 1 or FIG. 2. For the smallest input signal s79A provided by the first test article 79A a first margin M1 is then determined in a suitable way.

As an example the first margin M1 is determined by dividing the input signal s79A by a selected factor, e.g. 10. By subtracting the margin M1 from the measured amplitude of the input signal s79A the first threshold th1 is determined.

The determined first threshold th1 is stored in the control unit 5 for future application. The second margin M2 for the input signal s*79A recorded by moving the first test article 97A along the test axis ta is determined by multiplying the first margin M1 by the ratio of the amplitudes of the input signals s*79A and s79A.

In the diagram of FIG. 4 it is shown that in a preferred embodiment thresholds th22 and th23 are also determined for the signals provided by further test articles 79B, 79C. With the thresholds th21, th22 and th23 and the corresponding set of test articles 79A, 79B, 79C, the inventive metal detection apparatus 9 can thoroughly be tested for al materials of interest.

Figure 5A:
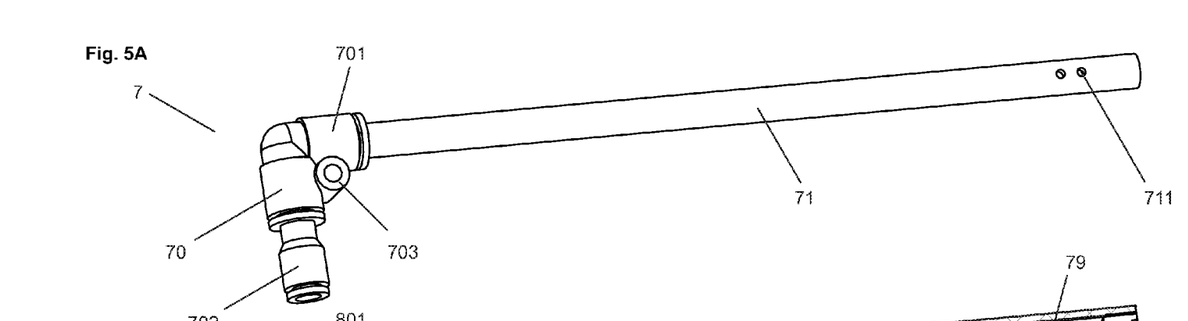
FIG. 5A shows a test device 7 that comprises a guide tube 71 that is connected to a fitting 70 and that encloses a test article 79 embedded in a slug 78 as shown in FIG. 5B.
Figures 5B, 5C:
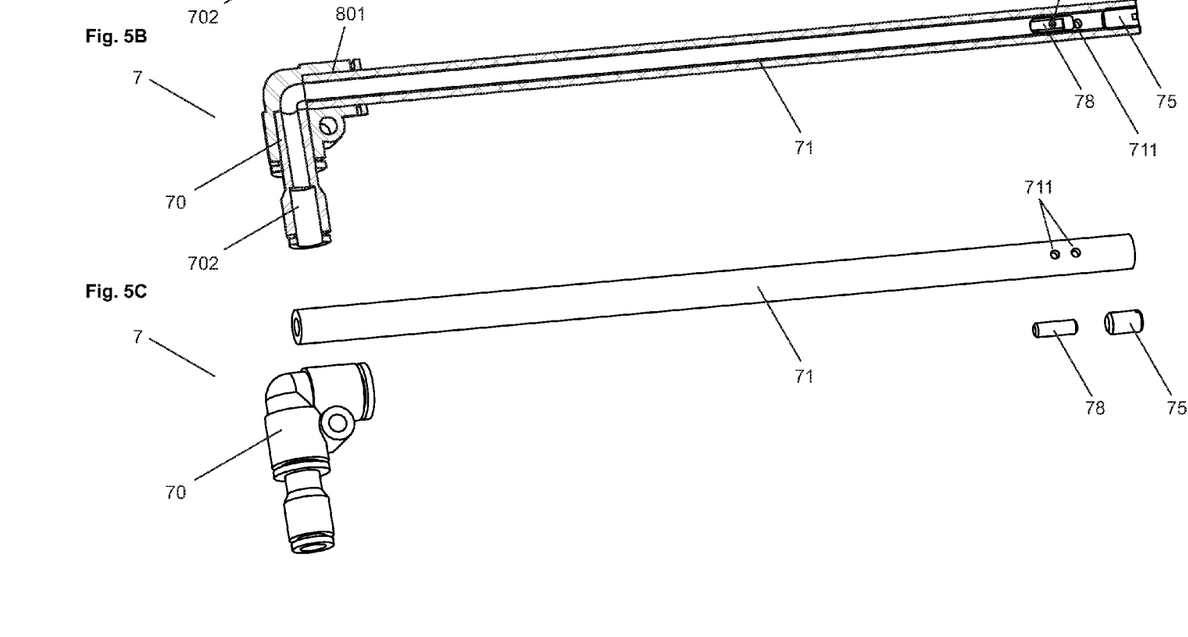
FIG. 5B shows a sectional view of the test device 7 of FIG. 5A that has been cut in a plane along the centre axis of the guide tube 71 and the fitting 70.
FIG. 5C shows the test device 7 of FIG. 5A in explosion view.

FIG. 5A and FIG. 5B show an example of a test device 7 in spatial view and in sectional view. FIG. 5C shows the test device 7 of FIG. 5A in explosion view. The test device 7 comprises a hollow cylindrical guide tube 71 that at the proximal end is connected to a fitting 70 and that encloses a test article 7 embedded in a slug 78. At the distal end the guide tube 71 is provided with a ventilation port 711 having two exhaust holes and with a threading, into which an end stop 75 is inserted, which may be a threaded bolt. The end stop 75 acts as end stop for the slug 78 and can preferably be adjusted in order to reach a desired length of the travelling path of the slug 78. The angular fitting 70 comprises a first fitting part 701, in which the guide tube 71 is held, and a second fitting part 702, which can be connected to a pneumatic coupling or directly to an air hose. By the application of air pressure, vacuum or gravitational force, the slug 78 can be moved forth and back between the proximal end and the distal end of the guide tube 71.

Figure 6:
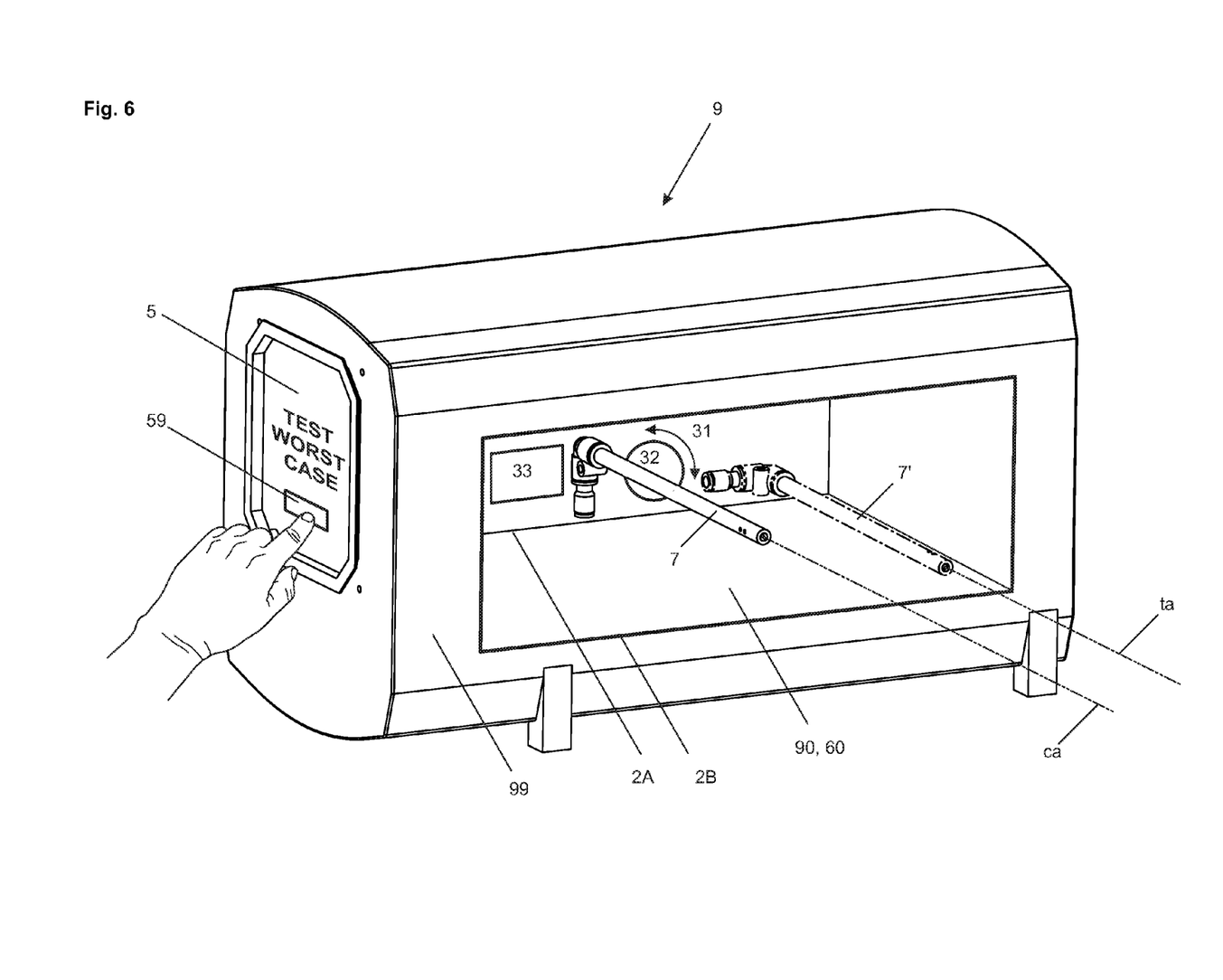
FIG. 6 shows the metal detection apparatus 9 of FIG. 2 equipped with a holding device 31 and a drive device 32 with which a test device 7 is movable between a first position, in which the test article 79 is movable along the centre axis ca of the transfer channel 90, and a second position, in which the test article 79 is movable along a test axis ta.

FIG. 6 shows the metal detection apparatus 9 of FIG. 2 equipped with a holding device 31 and a drive device 32 with which a test device 7 is movable between a first position, in which the test article 79 is movable along the centre axis ca of the detection zone 60, and a second position, in which the test article 79 is movable along a test axis ta located at the periphery of the detection zone 60. Since the test device 7 is presently aligned with the centre axis ca it is shown in dashed lines in the second position. In this preferred embodiment, the drive device 32 is operated under the control of the control unit 5 so at the test device 7 can be moved to a desired position, for which a threshold th1 or th2 is determined and applied. With the determined thresholds th1 or th2 future tests can automatically be executed with the same or identical test articles 79. However, tests can be executed automatically or under the control of the user, who may enter commands by touching command fields displayed the touch panel of the control unit 5 and/or manually move the test device 7.

The position of the test device 7 can also be detected by a position sensor 33. In the event that the test device 7 is moved manually and independently from the control unit 5, then the position sensor 33 will provide a signal to the control unit 5 as soon as the test device 7 has been moved to the related position, e.g. the position of the centre axis.

Figure 7:
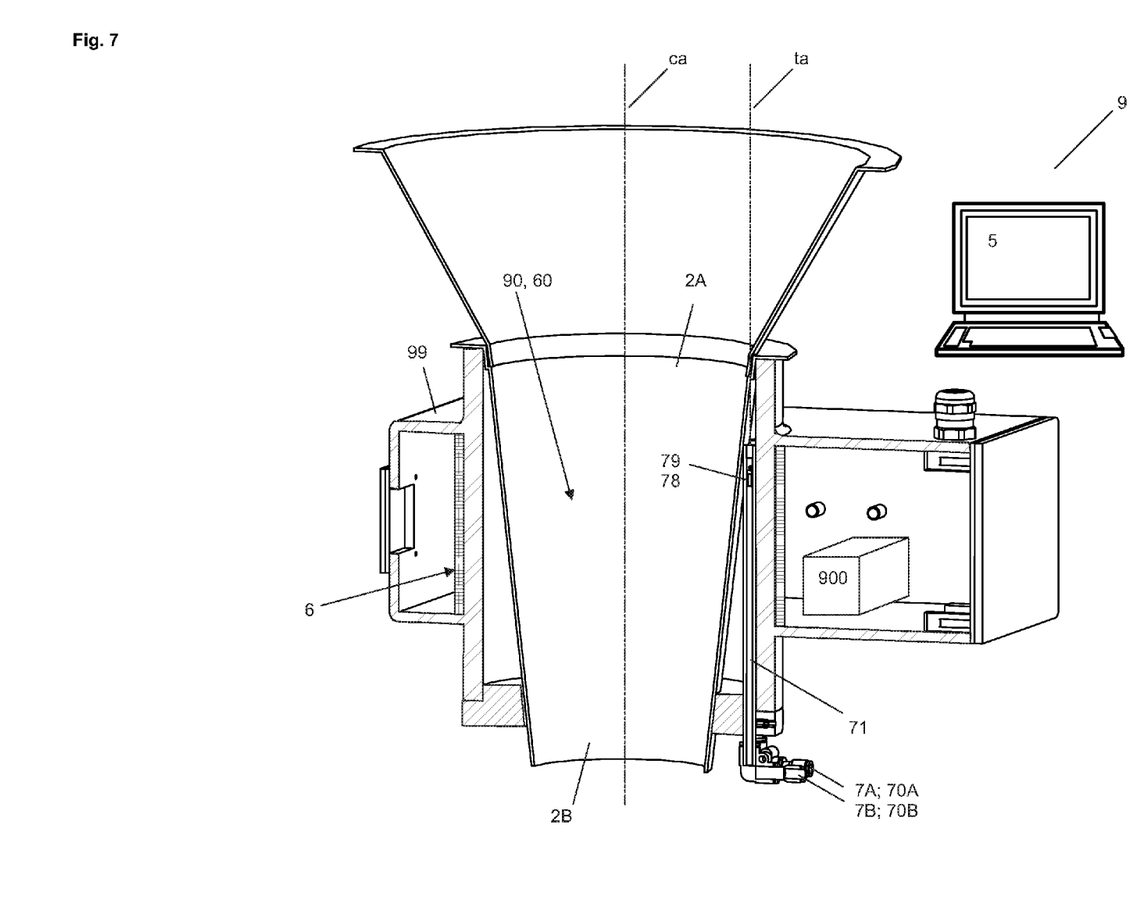
FIG. 7 shows a sectional view of an inventive metal detection apparatus 9 that comprises a conical transfer channel 90.

As stated above, the inventive method can be implemented in any metal detection apparatus. FIG. 7 shows a sectional view of an inventive metal detection apparatus 9 that comprises a conical transfer channel 90. This metal detection apparatus 9 is designed to detect metal contaminated product in vertical packaging applications, i.e. for the inspection of in-flight product prior to insertion into sealed packs. The apparatus is designed for minimised height allowing it to be installed for example in a restricted space between weigher and bag maker.

The metal detection apparatus 1 comprises an enclosure 99, having entrance and exit apertures 2A, 2B, which delimit the conical transfer channel 90 through which products P can be moved.

The metal detection apparatus 9 is equipped with a control unit 5 that may be connected to a centralised computer system. The metal detection apparatus 9 may operate autonomously or under the control of the centralised computer system, which may control one or a plurality of metal detection apparatuses 9 and may provide application parameters and gather measurement results.

For propelling the test articles, a pneumatic control device 900 is provided that preferably comprises pneumatic devices such as pressure generators, vacuum generators and valve means (not shown) which may be operated manually or under the control of the local control unit 5 or the centralised computer system via a control bus. The pneumatic control device 900 may comprise for example one or more air pumps and/or one or more vacuum generators operating for example according to the Venturi principle. The pressure and vacuum generators are preferably equipped with control or switching means for allowing pulsed application of a specific pressure or vacuum. Pneumatic equipment and devices for controlling this pneumatic equipment are available e.g. from Festo AG (see www.festo.us). The pneumatic control device 900 is designed to provide pressure or vacuum preferably in pulses to the fitting parts 702 of the test devices in selected test intervals, e.g., every 15 or 30 minutes.

What is claimed is:

1. A method for testing the sensitivity of an apparatus for detecting metal in a product, the apparatus having entrance and exit apertures which adjoin a transfer channel, along which the product moves through a coil system that defines a detection zone, the apparatus comprising a transmitter coil, a first receiver coil and a second receiver coil, the coils dimensioned such that a current applied to the transmitter coil induces a first coil signal in the first receiver coil and a second coil signal in the second receiver coil, wherein the respective induced coil signals do not compensate one another when metal is present in the product being transferred, resulting in an input signal within a signal processing path of the metal detection apparatus, the method comprising the steps of:

provide a test device with at least one test article arranged for movement through the detection zone;

moving the at least one test article through the detection zone along a first transfer axis (ca) and measuring a first input signal resulting therefrom;

moving the same at least one test article through the detection zone along at least one further transfer axis (ta; . . . ) and measuring a further input signal for each of the further transfer axes;

determining a first threshold (th1) adapted to the test article moved along the first transfer axis (ca) such that the amplitude of the first input signal exceeds the first threshold (th1);

determining a further threshold (th2; . . . ) associated with each of the at least one further transfer axes (ta, . . . ) along which the test article was moved, such that the amplitude of each of the at least one further input signal exceeds the associated further threshold (th2; . . . ); and selecting the respective first or further threshold (th1; th2; . . . ) in the signal processing path whenever the test article is moved along the associated first or further transfer axis (ca; ta; . . . ).

2. The method of claim 1, further comprising the steps of:

moving at least one further test article, having different properties than the at least one test article, along at least one of the transfer axes in a region of the detection zone where a specific sensitivity is present; and determining a further threshold associated with the further test article for the associated transfer axis provides the input signal with the smallest amplitude or for each of the at least one test articles.

3. The method of claim 2, wherein the first test article and each of the at least one further test articles differ in composition from each other.

4. The method of claim 1, wherein a threshold is determined at each of a first and a second operating frequency for at least the first test article as moved along at least one transfer axis.

5. The method of claim 1, wherein:

the first threshold is determined for the first transfer axis, for which the test article provides the input signal with the smallest amplitude; and the further thresholds for the respective further transfer axes are determined by either:

depending on a first margin by which the first threshold had been exceeded by the signal amplitude; or depending on the first threshold.

6. The method of claim 5, wherein:

the further thresholds for the further transfer axes are determined by multiplying the first threshold with a weighting factor q, which preferably corresponds to the ratio of the amplitudes of the input signals measured for the related further transfer axis compared to the amplitude of the input signal measured for the first transfer axis (ca).

7. The method of claim 5, wherein:

the thresholds for the further transfer axes are determined by multiplying the first margin (M1) with a weighting factor q, which preferably corresponds to the ratio of the amplitudes of the input signals measured for the related further transfer axis compared to the amplitude of the input signal measured for the first transfer axis, thus obtaining a second or further margin (M2, M3; . . . ) by which the input signals measured for the related further transfer axis exceed the further threshold.

8. The method of claim 1, wherein:

the first transfer axis is the center axis of the detection zone and extends from the entrance aperture to the exit aperture of the apparatus; and the further transfer axes are arranged equidistant from the first axis and are arranged in parallel with, or are equally inclined relative to, the first transfer axis.

9. The method of claim 1, wherein:

the coil system defines a conical or cylindrical detection zone or a detection zone with a rectangular cross-section, in which one or a plurality of different test articles are moved along the first transfer axis or along the further transfer axis, which is a test axis located inside or outside the coil system peripherally to the detection zone.

10. The method of claim 1, wherein:

the test device comprises a guiding device, that guides the test article along the related first or further transfer axis; and a test device is assigned to every transfer axis or a single test device is movable or moved between at least two of the transfer axes; and the guiding device is preferably a tube, in which the test article is moved back and forth along the assigned transfer axis by air pressure and/or gravity.

11. The method of claim 1, wherein the test device is mounted on a holding device with which the test device is moved between a first position, in which the test article is movable along the first transfer axis, and a second or further position, in which the test article is movable along the further transfer axis.

12. The method of claim 11, wherein the holding device is coupled to a drive unit, with which the holding device is movable or moved manually or automatically between the first and further position.

13. The method of claim 11, wherein the apparatus further comprises a control unit, with which the drive unit is controlled and/or the first or further threshold is applied in the signal processing path according to the position of the test device.

14. The method of claim 1, wherein the apparatus further comprises at least one position sensor, senses the position of the test device and send a signal to a control unit, which selects the first or further threshold in the signal processing path whenever the test article is moved along the related first or further transfer axis.

15. A metal detection apparatus, operating according to the method defined in claim 1, the apparatus comprising:

at least one test device with at least one test article; and a control unit, with which a first or further threshold is selectable and applicable in the signal processing path whenever a test article is movable or moved along a related first or further transfer axis for which the first or further threshold had been determined.

16. The metal detection apparatus of claim 15, further comprising a test device that is manually or automatically movable preferably under the control of the control unit between two or more positions, in which the test article is movable along the related first, second or further transfer axis.

* * * * *